United States Patent [19]
Timmerman et al.

[11] Patent Number: 6,117,886
[45] Date of Patent: Sep. 12, 2000

[54] TETRAZOLE DERIVATIVES

[75] Inventors: Hendrik Timmerman, Voorschoten, Netherlands; Mingqiang Zang, Scotland, United Kingdom; Kazuhiro Onogi, Iruma, Japan; Takeo Deushi, Sayama, Japan; Masahiro Tamura; Tsutomu Tohma, both of Higashimurayama, Japan; Yasushi Wada, Tachikawa, Japan; Jiro Matsumoto, Sayama, Japan; Toru Kanke, Higashimurayama, Japan

[73] Assignee: Kowa Co., Ltd., Nagoya, Japan

[21] Appl. No.: 09/357,156

[22] Filed: Jul. 19, 1999

Related U.S. Application Data

[62] Division of application No. 09/158,774, Sep. 23, 1998.

[30] Foreign Application Priority Data

Sep. 26, 1997 [JP] Japan .................... 9-262356

[51] Int. Cl.[7] ............. A61K 31/4709; A61P 11/06; C07D 401/14
[52] U.S. Cl. ........................... 514/312; 546/157
[58] Field of Search .............. 546/157; 514/312

[56] References Cited

U.S. PATENT DOCUMENTS

| 5,756,518 | 5/1998 | Timmerman et al. |
| 5,885,987 | 3/1999 | Timmerman et al. |

FOREIGN PATENT DOCUMENTS

| WO 89/05294 | 6/1989 | WIPO |
| 0 658 554 A1 | 6/1995 | WIPO |

*Primary Examiner*—Patricia L. Morris
*Attorney, Agent, or Firm*—Oblon, Spivak, McClelland, Maier & Neustadt, P.C.

[57] ABSTRACT

The present invention is directed to a tetrazole derivative represented by the following formula (1) or a salt thereof:

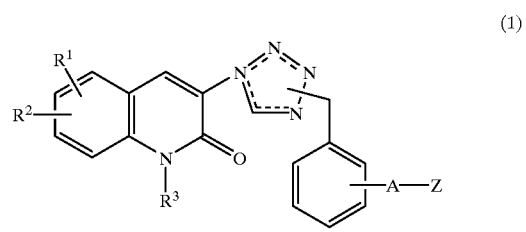

(1)

wherein $R^1$ and $R^2$ independently represent a hydrogen atom, a hydroxyl group, a lower alkyl group, a substituted or unsubstituted alkoxy group, or a substituted or unsubstituted alkanoyloxy group; $R^3$ represents a hydrogen atom or a substituted or unsubstituted lower alkyl group; A represents a methyleneoxy group or a vinylene group; Z represents a substituted or unsubstituted benzimidazolyl group; and a broken line indicates that there may be a double bond; and to a medicine containing the compound as an active ingredient. The medicine according to the present invention is endowed with excellent antileukotriene activity and antihistaminic activity, and is useful for the prevention and treatment of, for example, asthma.

11 Claims, No Drawings

TETRAZOLE DERIVATIVES

This application is a Divisional of U.S. application Ser. No. 09/158,744, filed on Sep. 23, 1998.

BACKGROUND OF THE INVENTION

1. Field of the Invention

The present invention relates to a tetrazole derivative and salts thereof, which have excellent antileukotriene activity and antihistaminic activity and are useful as a medicine for a broad range of allergic diseases.

2. Background Art

Leukotrienes (LTs) participate in most inflammatory diseases, including asthma, psoriasis, rheumatism, and inflammatory colitis, and play an important role in inflammation caused by cytotoxic reactions.

Thus, on the basis of the finding that leukotrienes are predominant mediators in allergic reactions and inflammations, there have been discovered, in an attempt to relieve these pathological conditions, an number of substances that suppress the action or the synthesis of leukotrienes (S. T. Holgate et al.: J. Allergy Clin. Immunol. 98, 1–13 (1996)).

Leukotrienes are arachidonic acid metabolites synthesized by 5-lipoxygenase (5-LO) and are divided into two groups. One group refers to $LTB_4$ and exhibits strong chemotaxis towards leukocytes. The other group collectively encompasses cysteine leukotrienes (CysLTs), including $LTC_4$, $LTD_4$, and $LTE_4$; these substances have long been called "slow-reacting substances of anaphylaxis (SRS-A)." In human tissues, CysLTs exert actions when they are coupled with their receptors. It has been found that a selective $LTD_4$ receptor inhibitor suppresses the contracting action of both $LTC_4$ and $LTD_4$ in human lung tissue, suggesting that the binding site of an $LTD_4$ receptor for $LTD_4$ also serves as a binding site for $LTC_4$ (Buckner C. K. et al.: Ann. NY Acad. Sci. 1988, 524; 181–6, Aharony D. et al.: New Trends in Lipid Mediators Research, Basel: Karger 1989; 67–71). $LTE_4$ is also considered to exert its action by the mediation of the same receptor available for $LTD_4$. However, since its activity is low, $LTE_4$ is considered a partially active substance.

Meanwhile, histamine contracts bronchial smooth muscle and promotes capillary permeability when coupled to an $H_1$ receptor prevailing in the cell membrane, and thus is considered a significant mediator in allergic diseases. More specifically, histamine is considered to trigger aggravation of various symptoms of asthma due to its bronchial contracting action, and is also considered to increase leakage of blood components into intercellular space due to its capillary permeation promotion action, to thereby participate in the onset mechanism of allergic rhinitis and the formation of edema in conjunctivitis, etc. Antihistaminic agents have been used in the treatment of allergic diseases as mentioned above. However, conventional antihistaminic agents involve the fear of causing adverse side effects to the central nervous system, such as drowsiness, when such an agent is coupled to an $H_1$ receptor in the brain. In recent years, bronchial asthma has been considered a chronic airway inflammation in which eosinocytes participate. In this connection, attention has been drawn to a delayed response which manifests airway constriction unique to asthma, as a result of infiltration of inflammation cells into bronchial mucosa and hypersecretion from the mucosa.

Briefly, in allergic diseases such as asthma, pathological profiles of immediate asthma response—i.e., bronchoconstriction and formation of edema in which histamine and similar mediators participate—and those of late asthma response—i.e., airway constriction that results from cellular infiltration, mucous secretion, hyperplasia of membrane, etc. in which leukotrienes participate—are deemed to play a significant role in the manifestation of pathological conditions. Similarly, the pathological profile of allergic rhinitis also comes to be elucidated as a two-phase reaction including an immediate asthma response phase manifesting ptarmus and hypersecretion of pituita, and a late asthma response phase manifesting nasal congestion due to swelling of the nasal membrane; wherein histamine participates in the former and leukotriene participates in the latter.

Accordingly, it is considered that a compound which exhibits antagonism against both a histamine $H_1$ receptor and an $LTD_4$ receptor and which minimally migrates into the brain can serve as a medicine having reduced side effects and can be effective for the prevention and treatment of a variety of symptoms from the instant response phase to the delayed response phase of a broad range of allergic diseases; in particular, asthma and rhinitis.

However, until realization of the present invention, a compound exhibiting sufficient antagonism against both the $LTD_4$ receptor—which relates to the late asthma response phase—and the histamine $H_1$ receptor—which relates to the immediate asthma response phase—had not yet been found. Moreover, many $LTD_4$ antagonists which are now being developed have at least one acid group in the molecule and are hydrophilic compounds having high polarity; inevitably they are not sufficiently absorbed by the oral route, leading to an increase in dose of these types of drugs and causing side effects.

SUMMARY OF THE INVENTION

In view of the foregoing, the present inventors have conducted extensive studies in search of a compound which has both anti-leukotriene activity and antihistaminic activity and which does not have the aforementioned drawbacks, and have found that the compound represented by the following formula (1) satisfactorily meets the present purposes, to thereby complete the present invention.

Accordingly, an object of the present invention is to provide an novel compound which has antihistaminic activity and anti-leukotriene activity, which minimally migrates into the brain, and which has no acid group in the molecule.

In one aspect of the present invention, there is provided a tetrazole derivative or a salt thereof represented by the following formula (1):

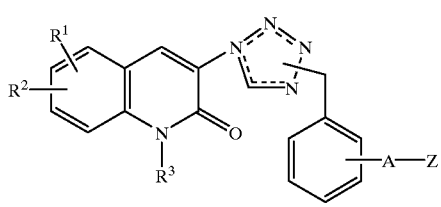

(1)

wherein $R^1$ and $R^2$ independently represent a hydrogen atom, a hydroxyl group, a lower alkyl group, a substituted or unsubstituted alkoxy group, or a substituted or unsubstituted alkanoyloxy group; $R^3$ represents a hydrogen atom or a substituted or unsubstituted lower alkyl group; A represents a methyleneoxy group or a vinylene group; Z represents a substituted or unsubstituted quinolyl group, a substituted or unsubstituted quinazolyl group, or a substituted or unsubstituted benzimidazolyl group; and a broken line indicates that there may be a double bond.

In another aspect of the present invention, there is provided a medicine comprising as an active ingredient a tetrazole derivative represented by the above-described formula (1) or a salt thereof.

In still another aspect of the present invention, there is provided a pharmaceutical composition comprising a tetrazole derivative represented by the above-described formula (1) or a salt thereof, and a pharmacologically acceptable carrier.

In yet another aspect of the present invention, there is provided use, as a medicine, of a tetrazole derivative represented by the above-described formula (1) or a salt thereof.

In yet another aspect of the present invention, there is provided a method for the treatment of allergic diseases, which method comprises administering to a patient in need thereof an effective amount of a tetrazole derivative represented by the above-described formula (1) or a salt thereof.

In yet another object of the present invention, there is provided a method for the treatment of a disease selected from the group consisting of asthma, allergic rhinitis, allergic conjunctivitis, atopic dermatitis, urticaria, psoriasis, rheumatism, inflammatory colitis, cerebral ischemia, and cerebral apoplexy, which method comprises administering to a patient in need thereof an effective amount of a tetrazole derivative represented by the above-described formula (1) or a salt thereof.

BEST MODE FOR CARRYING OUT THE INVENTION

In the tetrazole derivative of formula (1), the lower alkyl groups represented by $R^1$ or $R^2$ include C1–C6 linear or branched alkyl groups. Specific examples thereof include a methyl group, an ethyl group, a n-propyl group, an i-propyl group, a n-butyl group, an i-butyl group, a sec-butyl group, a t-butyl group, a pentyl group, and a hexyl group. Of these groups, a methyl group and a t-butyl group are particularly preferred. The alkoxy group may be linear or branched and may have 1–6 carbon atoms. Examples of preferred alkoxy groups include a methoxy group, an ethoxy group, a n-propoxy group, an i-propoxy group, a butoxy group, a pentyloxy group, and a hexyloxy group. Of these, a methoxy group, an ethoxy group and a n-propoxy group are particularly preferred. The alkoxy groups may have substituents. Examples of the substituents include an alkoxy group; a halogen atom; a phenyl group which may have a substituent such as a quinolyl methoxy group; a piperazinyl group which may have a substituent such as a methyl group or a quinolylmethyl group; and a di-(C1–C4)alkylamino group such as a dimethylamino group or a diethylamino group. The alkanoyloxy group preferably has 2 to 5 carbon atoms; for example, mention may be given of an acetyloxy group, a propionyloxy group, and an n-butylyloxy group. The alkanoyloxy group may have a substituent such as an amino group.

In the formula, the lower alkyl groups represented by $R^3$ include C1–C6 linear or branched alkyl groups. Specific examples thereof include a methyl group, an ethyl group, an n-propyl group, an i-propyl group, a n-butyl group, an i-butyl group, a sec-butyl group, a t-butyl group, a pentyl group, and a hexyl group. Of these groups, a methyl group is particularly preferred. The lower alkyl groups may have substituents. Examples of the substituents include a halogen atom, an amino group, a phenyl group, and a heterocyclic group such as a piperazinyl group. These substituents may further have substituents such as a C1–C4 alkyl group, e.g., methyl or ethyl; a quinolyl C1–C4 alkoxy group, e.g., a quinolyl methoxy group; a benzimidazolyl C1–C4 alkoxy group, e.g., a benzimidazolyl methoxy group; or a quinolyl C1–C4 alkyl group, e.g., a quinolyl methyl group. Preferably, $R^3$ is a hydrogen atom, a methyl group, a dimethylaminomethyl group, or a 3-[4-(2-quinolylmethyl) piperazinyl]propyl group.

Examples of groups represented by Z include a quinolyl group, a quinazolyl group, and a benzimidazolyl group; these groups may have substituents. Examples of the substituents include a C1–C4 alkyl group, e.g., a methyl group or an ethyl group; and a (C1–C4)alkoxy(C1–C4)alkyl group, e.g., an ethoxyethyl group or a methoxymethyl group.

No particular limitation is imposed on the salts of the compounds of the present invention represented by formula (1), so long as they are pharmacologically acceptable. Examples of such salts include acid addition salts of mineral acids, such as hydrochlorides, hydrobromides, hydroiodides, sulfates, and phosphates; and acid addition salts of organic acids, such as benzoates, methanesulfonates, ethanesulfonates, benzenesulfonates, p-toluenesulfonates, oxalates, maleates, fumarates, tartarates and citrates.

The compound of formula (1) of the present invention (hereinafter may be referred to as compound (1)) may take the form of a solvate such as a hydrate, and the present invention encompasses such a solvate.

Also, the compound (1) may take the form of a ketoenol tautomer, and the present invention encompasses such a tautomer.

The compound (1) of the present invention may be prepared by, for example, the methods described below.

Method A

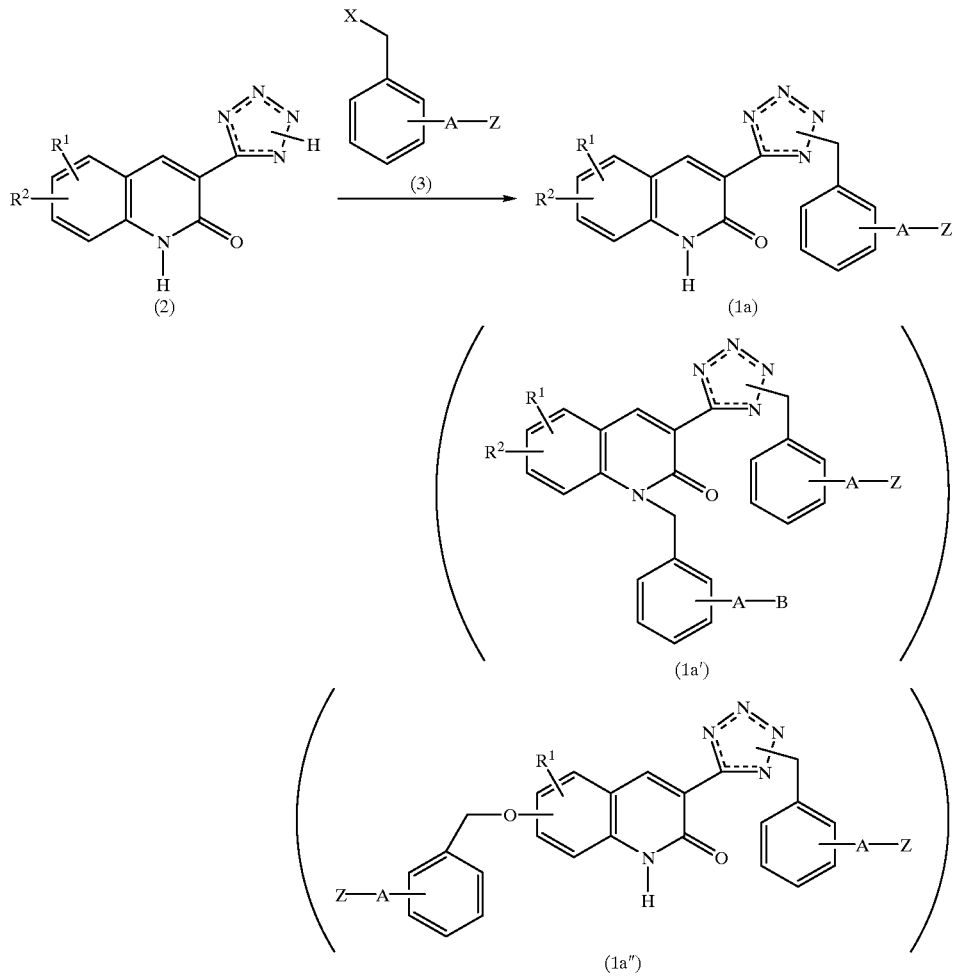

wherein X represents a halogen atom, and $R^1$, $R^2$, A, and B have the same meanings as described above.

Briefly, the compound (1a) of the present invention in which $R^1$ and $R^2$ independently represent a hydrogen atom, a hydroxyl group, a lower alkyl group, or a lower alkoxyl group may be prepared, as shown in Method A, by causing a reaction between a tetrazolylquinolinone compound (2) and a halogen compound (3) in an amount of one equivalent, in the presence of an excessive amount of a base such as sodium carbonate or potassium carbonate, in an aprotic polar solvent such as dimethylformamide (DMF), dimethylsulfoxide (DMSO), or hexamethylphosphoramide (HMPA) within a temperature range of 0° C. to a reflux temperature (preferably from room temperature to 80° C.) for 1–7 days. In the case in which neither $R^1$ nor $R^2$ is a hydroxyl group, a compound (1a') of the present invention wherein $R^3$ is a Z—A-benzyl group may be by-produced, whereas in the case in which $R^1$ and/or $R^2$ is a hydroxyl group, there may be by-produced a compound (1a") of the present invention wherein the hydrogen of the hydroxyl group has been substituted by a Z—A-benzyl group. For this reason, in order to obtain a compound (1) of the present invention in which $R^1$ and/or $R^2$ is a hydroxyl group, the hydroxyl group of the compound (2) is protected by use of an appropriate protective group, followed by removal of the protection (Method B).

Method C.D

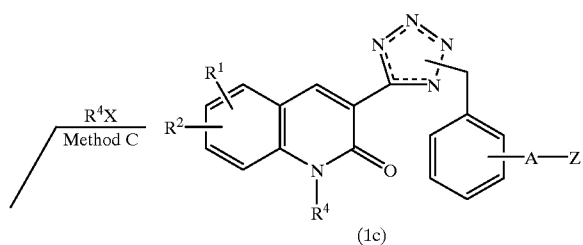

-continued

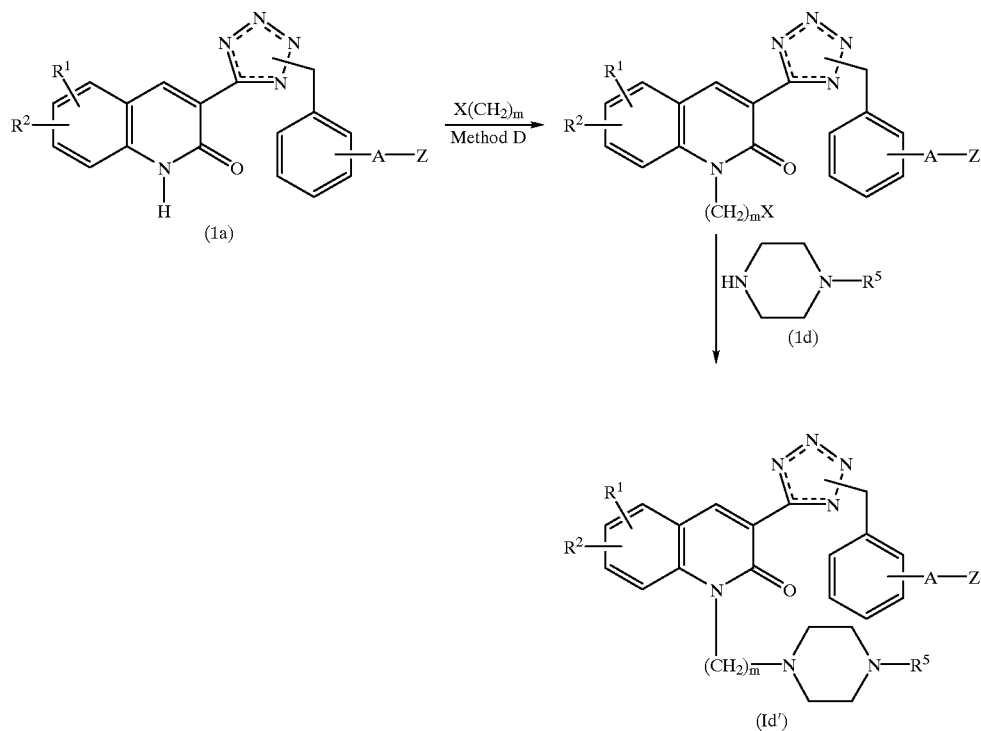

wherein $R^1$, $R^2$, A, Z, and X have the same meanings as described above, $R^4$ represents a lower alkyl group which may have a substituent, $R^5$ represents a lower alkyl group which may have a substituent, and m is an number between 1 and 4 inclusive.

Alkylation of the compound (1a) transforms the compound (1a) into a compound (1c) of the present invention in which $R^3$ is a substituted or unsubstituted lower alkyl group ($R^4$) (Method C). Alternatively, haloalkylation transforms the compound (1a) into a compound (1d), which may further be piperazinylated to a compound (1d') of the present invention (Method D).

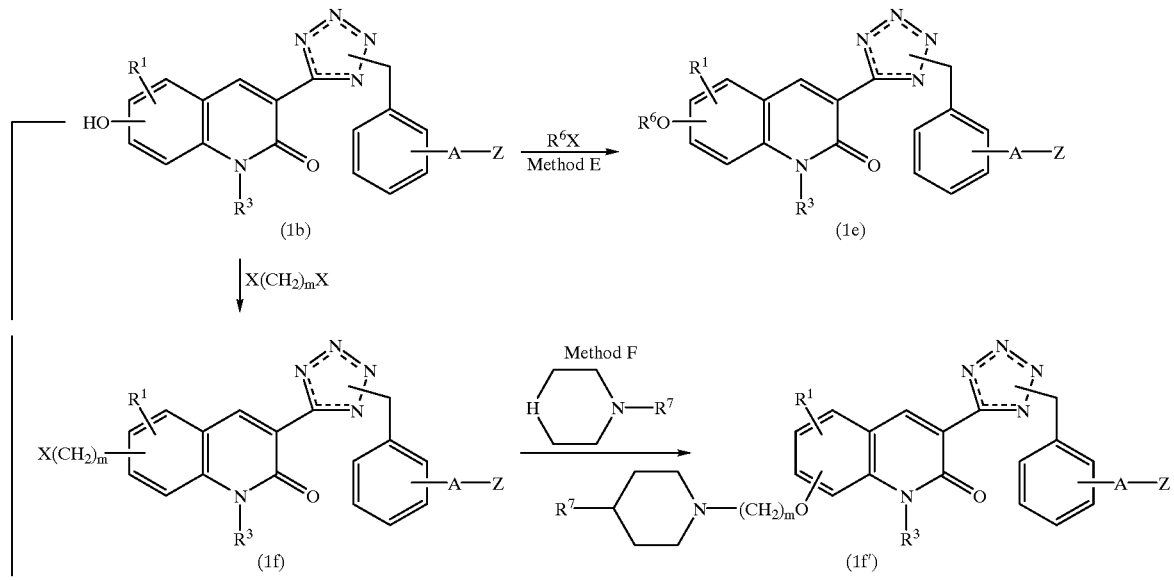

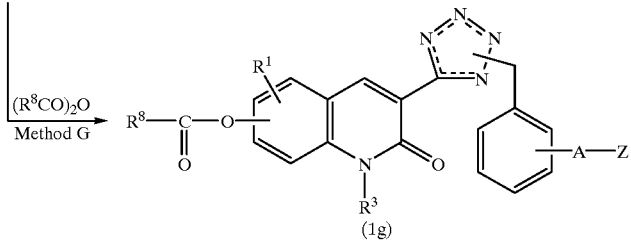

(1g)

wherein $R^1$, $R^3$, A, Z, X, and m have the same meanings as defined above, $R^6$ represents a dialkylaminoalkyl group, $R^7$ represents a lower alkyl group, and $R^8$ represents an alkyl group.

The compound (1e) of the present invention in which $R^2$ is a dialkylaminoalkoxy group is obtained through diaminoalkylation of the compound (1b) in which $R^2$ is a hydroxyl group (Method E). Also, the compound (1f) of the present invention in which $R^2$ is a piperazinylalkoxy group is obtained by haloalkylation of compound (1b) and by subsequent piperazinylation of the resultant compound (1f) (Method F). The compound (1g) of the present invention in which $R^2$ is an alkylcarbonyloxy group is obtained through esterification of the hydroxyl group of compound (1b) (Method G).

Independently, the aforementioned compound (2), which serves as a raw material of the compound (1) of the present invention may be formed as follows. Briefly, a cyanoquinoline compound (4) is first formed according to a known method, e.g., a method described by Bhaduri, Amiya Prasad et al.; J. Heterocyclic Chem., 23, 409–411, 1985, then the cyanoquinoline compound (4) is reacted with an azide compound such as sodium azide, in an aprotic polar solvent such as DMF, DMSO, or HMPA, in the presence of ammonium chloride, at a temperature between 0° C. and 200° C. inclusive, preferably between room temperature to 120° C. inclusive, for several hours to one day.

Method H

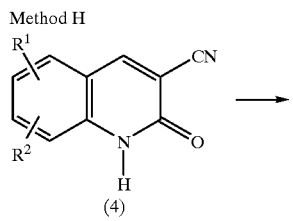

(4)

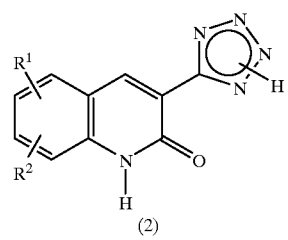

(2)

wherein $R^1$ and $R^2$ have the same meanings as defined above.

Among several compounds of formula (3) which serve as another raw materials, the halogen compounds of formulas (3a) to (3c) may be prepared, for example, by the following processes.

The halogen compound (3a) may be commercially obtained, or may be prepared in accordance with a method described, for example, by Musser, John H. et al.; J. Med. Chem. 33(1), 240–245, 1990 or by Iemura, Ryuichi et al.; J. Heterocyclic. Chem. 24(1), 31–37, 1987.

The halogen compounds (3b) and (3c) may be prepared, for example, by the following method.

Method I

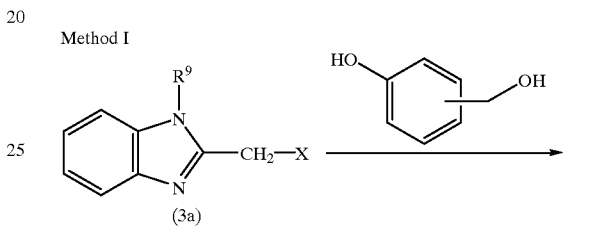

(3a)

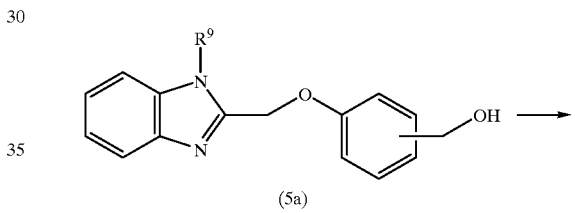

(5a)

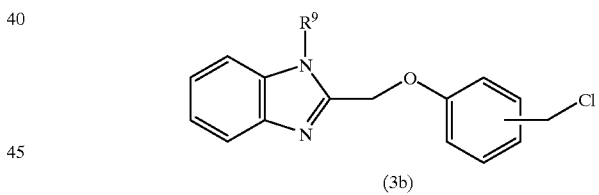

(3b)

Method J

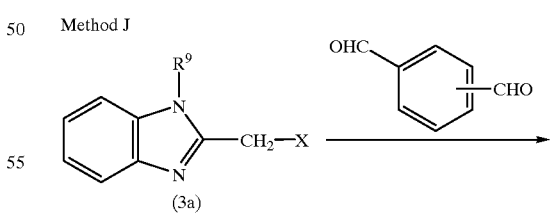

(3a)

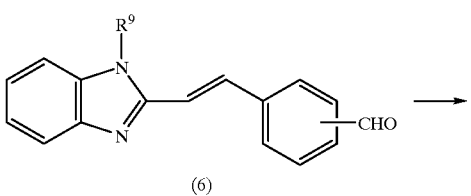

(6)

-continued

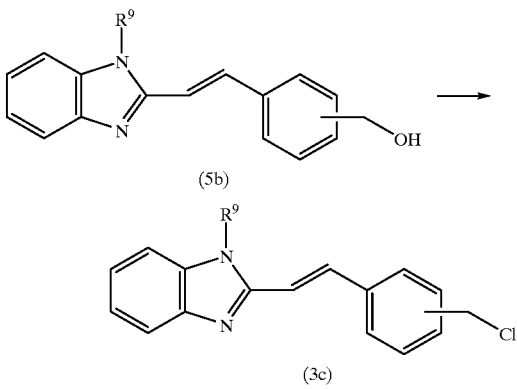

(5b)

(3c)

wherein R⁹ represents an alkyl group or a C1–C4 alkoxy C1–C4 alkyl group, and X represents a halogen atom.

When the halogen compound (3a) and hydroxybenzyl alcohol in an equivalent amount are allowed to react with each other in an aprotic polar solvent such as DMF, DMSO, or HMPA, in the presence of an excessive amount of amount of a base such as sodium carbonate or potassium carbonate, at a temperature between 0° C. and a reflux temperature inclusive, preferably between room temperature to 60° C. inclusive, for one to 7 days, there is obtained a benzyl alcohol (5a).

Independently, a benzyl alcohol of formula (5b) may be prepared as follows. The halogen (3a), together with an equivalent amount of PPh₃ (Ph stands for phenyl), is first refluxed in an inert solvent such as benzene, toluene, or xylene for 12–48 hours, to thereby synthesize a corresponding phosphonium salt. The phosphonium salt is allowed to react with an equimolar amount of t-BuOK (potassium tert-butoxide) in an absolute THF under nitrogen or argon, to thereby prepare a Wittig reagent. To the Wittig reagent are added equimolar amounts of phthalic aldehyde, isophthalic aldehyde, and terephthalic aldehyde, and the mixture is subjected to refluxing for 1 to 12 hours, to thereby obtain an aldehyde compound (6). The aldehyde compound (6) is then reacted with sodium borohalide in a protic polar solvent such as methanol or ethanol at a temperature between 0° C. and a reflux temperature inclusive, preferably at room temperature, for 1–24 hours, to thereby obtain the benzyl alcohol (5b).

The thus-obtained benzyl alcohol (5a) or (5b) is allowed to react with an excessive amount of thionyl chloride in an inert solvent such as THF, Chloroform, or methylene chloride, at a temperature between 0° C. and a reflux temperature inclusive, preferably at room temperature, for 1–24 hours, to thereby obtain a halogen compound (3b) or (3c).

After completion of the above-described sequence of reactions, a suitable treatment of the obtained compound according to a customary method provides a target compound (1) of the present invention, which may further be purified by a customary purification means such as recrystallization, column chromatography, etc., as desired. If necessary, the compound may be converted into any one of the aforementioned salts.

The thus-obtained compounds (1) and their salts of the present invention exhibit excellent anti-leukotriene activity and excellent antihistaminic activity, as demonstrated by the below-described examples, and are useful as remedies, including preventive drugs and therapeutic drugs, for asthma, allergic rhinitis, allergic conjunctivitis, atopic dermatitis, urticaria, psoriasis, rheumatism, inflammatory colitis, cerebral ischemia, and cerebral apoplexy.

The medicine of the present invention comprises as an active ingredient the above-described compound (1), a salt thereof, or a hydrate of the compound (1) or the salt. Examples of the manner of administration of the present medicine include oral administrations by way of tablets, capsules, granules, powders, and syrups and non-oral administrations such as intravenous injections, intramuscular injections, suppositories, inhalations, percutaneous absorptions, eye drops, and nasal drops. In order to prepare pharmaceutical preparations of a variety of forms, the aforementioned active ingredient may be used alone or in combination with a pharmaceutical vehicle, such as, for example, an excipient, a binder, a bulking agent, a disintegrant, a surfactant, a lubricant, a dispersing agent, a buffering agent, a preservative, a flavoring agent, a perfume, a coating agent carrier, a diluent, etc.

The dosage of the medicine of the present invention varies in accordance with the age, body weight, symptom, manner of administration, frequency of the administration, etc. In general, in the case of adults, it is preferred that the compound of the present invention be administered in an amount of 1–1,000 mg per day at a time or as divided in several times, orally or non-orally.

EXAMPLES

The present invention will next be described by way of examples, which should not be construed as limiting the invention thereto.

Production Example 1

Synthesis of 6-methoxy-3-tetrazolyl-1,2-dihydroquinolin-2-one sodium salt

3-Cyano-6-methoxy-1,2-dihydroquinolin-2-one (78.6 g, 393 mmol) was dissolved in DMF (1 liter), and ammonium chloride (83.8 g, 1.57 mol) and sodium azide (102.2 g, 1.57 mol) were added to the resultant mixture. The mixture was stirred for 12 hours at a bath temperature of 120° C. The reaction mixture was concentrated under reduced pressure. Subsequently, an 2N sodium hydroxide aqueous solution (800 ml) was added to the reaction mixture, and the mixture was heated. After removal of the insoluble matter by filtration, the filtrate was allowed to cool. The crystals that precipitated were collected, to thereby obtain the title compound as pale yellow needles (90.0 g, 339 mmol, 86.3%).

mp:>260° C.

$^1$H-NMR (DMSO-$d_6$) δ (ppm): 11.9 (1H, br), 8.45 (1H, s), 7.34 (1H, d, J=1.5 Hz), 7.30 (1H, d, J=8.8 Hz), 7.15 (1H, dd, J=8.8, 1.5 Hz), 3.80 (3H, s).

IR(KBr)cm$^{-1}$: 3445, 1665, 1624, 1510, 1461, 1368, 1234, 1171, 1034, 638.

Production Example 2

Synthesis of 6-tert-Butyl-3-tetrazolyl-1,2-dihydroquinolin-2-one 6-tert-Butyl-3-cyano-1,2-dihydroquinolin-2-one (1.74 g, 7.7 mmol) was dissolved in DMF (20 ml), and ammonium chloride (1.65 g, 30.8 mol) and sodium azide (2.00 g, 30.8 mol) were added to the resultant mixture. The mixture was stirred at a bath temperature of 120° C. for 16 hours. Water added to the reaction mixture. After removal of the precipitates by filtration, the reaction mixture was recrystallized from DMF-methanol. The crystals that precipitated were collected, to thereby obtain the title compound as yellow powder (1.08 g, 4.0 mmol, 52%).

mp: 280–286° C. (d.)

$^1$H-NMR (CDCl$_3$) δ (ppm): 8.96 (1H, s), 7.95 (1H, d, J=2.2 Hz), 7.75 (1H, dd, J=8.5, 2.2 Hz), 7.39 (1H, d, J=8.5 Hz), 1.34 (9H, s).

IR(KBr)cm$^{-1}$: 2964, 1667, 1625, 1535, 1473, 1365, 1261, 1156, 1036, 626

Production Examples 3 through 7

In a manner similar to that of Production Examples 1 and 2, the following compounds were obtained.

TABLE 1

| Ex. | Compound | Property | m.p. |
|---|---|---|---|
| 3 | 7-Hydroxy-3-tetrazolyl-1,2-dihydroquinolin-2-one | Brown powder | >280° C. |
| 4 | 8-Hydroxy-3-tetrazolyl-1,2-dihydroquinolin-2-one | Brown powder | >280° C. |
| 5 | Sodium 6-methoxymethoxy-3-tetrazolyl-1,2-dihydroquinolin-2-one | Pale yellow scales | >270° C. |
| 6 | 3-Tetrazolyl-1,2-dihydroquinolin-2-one | Pale yellow powder | >280° C. |
| 7 | 5-Ethoxy-8-methyl-3-tetrazolyl-1,2-dihydroquinolin-2-one | Yellow powder | 278–280° C. (d.) |

Production Example 8

Synthesis of 3-(2-quinolylmethoxy)benzyl chloride

To a solution of 3-(2-quinolylmethoxy)benzyl alcohol 3.58 g, 13.5 mmol) in CHCl$_3$ (100 ml) was added SOCl$_2$ (2 ml). The mixture was stirred at room temperature for 24 hours. A small amount of methanol was added to the reaction mixture, and the solvent thereof was removed under reduced pressure, to thereby obtain the title compound as white powder.

Production Example 9

Synthesis of 2-(2-quinazolylmethoxy)benzyl alcohol

To a solution of 2-Chloromethylquinazoline (5.00 g, 28 mmol) in DMF (50 ml) were added potassium carbonate (4.26 g, 31 mmol) and tetra-n-butylammoniumbromide (903 mg, 2.8 mmol). 3-Hydroxybenzylalcohol (3.48 g, 28 mmol) was added to the resultant mixture, and the mixture was stirred at room temperature for five days. Subsequently, the reaction mixture was concentrated under reduced pressure. Chloroform and water were added to the resultant mixture, and the organic phase was extracted from the mixture. The organic phase was dried over sodium sulfate anhydrate, concentrated under reduced pressure, and recrystallized from a chloroform-n-hexane mixture, to thereby obtain the title compound as pale yellow powder (6.94 g, yield: 93.1%).

mp: 92–96° C.

$^1$H-NMR(CDCl$_3$) δ (ppm): 9.43(1H, s, —C$_8$H$_5$N$_2$—), 8.07 (1H, d, J=9.0 Hz, —C$_8$H$_5$ N$_2$—), 7.95 (1H, d, J=7.5 Hz, —C$_8$H$_5$N$_2$—), 7.93 (1H, d, J=9.0 Hz, —C$_8$H$_5$N$_2$—), 7.67 (1H, dd, J=7.5, 7.5 Hz, —C$_8$H$_5$N$_2$—), 7.25 (1H, dd, J=7.8, 7.8 Hz, —C$_6$H$_4$—), 7.11 (1H, s, —C$_6$H$_4$—), 6.99 (1H, d, J=7.8 Hz, —C$_6$H$_4$—), 6.96 (1H, d, J=7.8 Hz, —C$_5$H$_4$—), 5.46 (2H, s, C$_8$H$_5$N$_2$—CH$_2$—), 4.65 (2H, s, —C$_6$H$_4$—CH$_2$—OH).

IR(KBr)cm$^{-1}$: 3328, 1621, 1613, 1582, 1441, 1378, 1292, 1077, 752.

Production Example 10

Synthesis of 3-(N-methylbenzimidazol-2-ylmethoxy)benzyl alcohol

In a manner similar to that of Production Example 9, the title compound was obtained as pale yellow needles by use of 2-chloromethyl-N-methylbenzimidazole (yield: 58.4%).

mp: 183–185° C.

$^1$H-NMR (CDCl$_3$) δ (ppm): 7.69 (1H, m, C$_8$H$_7$N$_2$—), 7.16–7.32 (4H, m, Ar—H), 7.02 (1H, s, —C$_6$H$_4$—), 6.88–6.94 (2H, m, —C$_6$H$_4$—), 5.29 (2H, s, C$_8$H$_7$N$_2$—CH$_2$—), 4.61 (2H, s, —C$_6$H$_4$—CH$_2$—OH), 3.81 (3H, s, N—CH$_3$).

IR(KBr)cm$^{-1}$: 2850, 1594, 1482, 1441, 1366, 1259, 1227, 1048, 1029, 750.

Production Example 11

Synthesis of 4-(2-N-methylbenzimidazol-2-ylmethoxy)benzyl alcohol

In a manner similar to that of Production Example 9, the title compound (yield: 46.7%) was obtained as pale yellow prisms by use of 2-Chloromethyl-N-methylbenzimidazole and 4-Hydroxybenzyl alcohol.

mp: 176–180° C.

$^1$H-NMR (CDCl$_3$) δ (ppm): 7.78 (1H, m, C$_8$H$_7$N$_2$—), 7.23–7.38 (3H, m, C$_8$H$_7$N$_2$—), 7.30 (2H, d, J=8.6 Hz, —C$_6$H$_4$—), 7.04 (2H, d, J=8.6 Hz, —C$_6$H$_4$—), 5.34 (2H, s, C$_8$H$_7$N$_2$—CH$_2$—), 4.62 (2H, s, —C$_6$H$_4$—CH$_2$—OH), 3.88 (3H, s, N—CH$_3$).

IR(KBr)cm$^{-1}$: 3174, 2846, 1607, 1585, 1507, 1484, 1240, 1047, 1030, 734.

Production Example 12

Synthesis of 3-[N-(2-ethoxyethyl)benzimidazol-2-ylmethoxy]benzyl alcohol

In a manner similar to that of Production Example 9, the title compound (yield: 90.3%) was obtained as colorless needles by use of 2-Chloromethyl-N-(2-ethoxyethyl)benzimidazole.

mp: 105–107° C.

$^1$H-NMR (CDCl$_3$) δ (ppm): 7.71 (1H, m, Ar—H), 7.41 (1H, m, Ar—H), 7.23–7.34 (3H, m, Ar—H), 7.11 (1H, s, —C$_6$H$_4$—), 6.96–7.62 (2H, m, —C$_6$H$_4$—), 5.43 (2H, s, C$_{11}$H$_{13}$N$_2$O—CH$_2$O—), 4.68 (2H, d, J=5.6 Hz, —C$_6$H$_4$—CH$_2$OH), 4.48 (2H, t, J=5.4 Hz, —CH$_2$—CH$_2$OCH$_2$CH$_3$), 3.74 (2H, t, J=5.4 Hz, —CH$_2$CH$_2$OCH$_2$CH$_3$), 3.39 (2H, q, J=6.8 Hz, CH$_2$CH$_2$OCH$_2$CH$_3$), 2.24 (1H, br, —C$_6$H$_4$—CH$_2$OH), 1.10 (3H, t, J=6.8 Hz, CH$_2$CH$_2$OCH$_2$CH$_3$).

IR(KBr)cm$^{-1}$: 2875, 1594, 1471, 1445, 1426, 1369, 1258, 1154, 1050, 1035, 761.

Production Example 13

Synthesis of 4-[N-(2-ethoxyethyl)benzimidazol-2-ylmethoxy]benzyl alcohol

In a manner similar to that of Production Example 9, the title compound (yield: 83.4%) was obtained as pale yellow prisms by use of 2-chloromethyl-N-(2-ethoxyethyl)benzimidazole and 4-Hydroxybenzyl alcohol.

mp: 90–92° C.

$^1$H-NMR (CDCl$_3$) δ (ppm): 7.78 (1H, m, Ar—H), 7.41 (1H, m, Ar—H), 7.25–7.34 (4H, m, Ar—H), 7.08 (2H, d, J=8.8 Hz, —C$_6$H$_4$—), 5.44 (2H, s, C$_{11}$H$_{13}$N$_2$O—CH$_2$O—), 4.62 (2H, d, J=5.7 Hz,—C$_6$H$_4$—CH$_2$—OH), 4.49 (2H, t, J=5.6 Hz, —CH$_2$—CH$_2$OCH$_2$CH$_3$), 3.75 (2H, t, J=5.6 Hz, —CH$_2$CH$_2$OCH$_2$CH$_3$), 3.39 (2H, q, J=7.1 Hz, CH$_2$CH$_2$OCH$_2$CH$_3$), 1.66 (1H, t, J=5.7 Hz, —C$_6$H$_4$—CH$_2$OH), 1.10 (3H, t, J=7.1 Hz, CH$_2$CH$_2$OCH$_2$CH$_3$).

IR (KBr) cm$^{-1}$: 3180, 2858, 1609, 1587, 1509, 1472, 1417, 1237, 1117, 1036, 747.

Production Example 14

Synthesis of 3-[2-(2-quinolyl)ethenyl]benzyl alcohol

3-[2-(2-quinolyl)ethenyl]benzyl aldehyde (25.92 g, 0.1 mol) was dissolved in methanol (300 ml). Sodium borohydride (7.57 g, 0.2 mol) was added to the resultant mixture, and the mixture was stirred at room temperature for one hour. The solvent of the reaction mixture was removed under reduced pressure. Water was added to the obtained residue, and the organic phase was extracted from the solution with ethyl acetate. The organic phase was dried over magnesium sulfate anhydrate, and recrystallized from ethyl acetate, to thereby obtain the title compound as pale yellow powder (21.42 g, 82.0 mmol, 82.0%).

Production Examples 15 Through 22

In a manner similar to that of Production Example 8, the following compounds were obtained.

TABLE 2

| Ex. | Compound | Property |
| --- | --- | --- |
| 15 | 4-(2-Quinolylmethoxy)benzyl chloride | White powder |
| 16 | 3-(2-Quinazolylmethoxy)benzyl chloride | White powder |
| 17 | 4-(2-Quinazolylmethoxy)benzyl chloride | White powder |
| 18 | 3-(2-N-Methylbenzimidazol-2-ylmethoxy)benzyl chloride | White powder |
| 19 | 4-(2-N-Methylbenzimidazol-2-ylmethoxy)benzyl chloride | White powder |
| 20 | 3-[N-(2-Ethoxyethyl)benzimidazol-2-ylmethoxy]benzyl chloride | Pale yellow oily material |
| 21 | 4-[N-(2-Ethoxyethyl)benzimidazol-2-ylmethoxy]benzyl chloride | Pale yellow oily material |
| 22 | 3-[2-(2-Quinolyl)ethenyl]benzyl chloride | White powder |

Examples 1 and 2

Synthesis of 6-methoxy-3-{2-[3-(2-quinolylmethoxy)benzyl]tetrazolyl}quinolin-2-one and 6-methoxy-3-{1-[3-(2-quinolylmethoxy)benzyl]tetrazolyl}quinolin-2-one To 6-methoxy-3-tetrazolyl-1,2-dihydroquinolin-2-one sodium salt (36.7 g, 138 mmol), sodium carbonate (14.7 g, 138 mmol), and tetra-n-butylammoniumbromide (22.3 g, 66.1 mmol), was added DMF (2 liters). (2-Quinolylmethoxy)benzyl chloride (58.7 g) was added to the resultant mixture, and the mixture was stirred for 15 hours at a bath temperature of 80° C. Subsequently, the solvent of the reaction mixture was removed under reduced pressure. To the obtained residue was added an 2N sodium hydroxide aqueous solution (1 liter). The organic phase was extracted from the solution with a mixture of chloroform-methanol (5:1). The organic phase was dried over sodium sulfate anhydrate, recrystallized from ethyl acetate, subjected to silica gel column chromatography (chloroform-methanol (5:1)), and concentrated under reduced pressure. The obtained residue was recrystallized from a chloroform-methanol-ether mixture, to thereby obtain crude 6-methoxy-3-{2-[3-(2-quinolylmethoxy)benzyl]tetrazolyl}quinolin-2-one as first-deposited crystals, and crude 6-methoxy-3-{1-[3-(2-quinolylmethoxy)benzyl]tetrazolyl}quinolin-2-one as second-deposited crystals.

The first-deposited crystals were further purified through recrystallization (with DMF-ether), to thereby obtain 6-methoxy-3-{2-[3-(2-quinolylmethoxy)benzyl]tetrazolyl}quinolin-2-one (24.0 g, yield: 35.4%) as yellow powder.

mp: 213–214° C. (d.)

$^1$H-NMR (DMSO-d$_6$) δ (ppm): 12.01 (1H, br), 8.56 (1H, s), 8.39 (1H, d, J=8.3 Hz), 8.00 (1H, d, J=7.8 Hz), 8.03–7.94 (2H, m), 7.76 (1H, ddd, J=8.3, 6.8, 1.5 Hz), 7.67 (1H, d, J=8.3 Hz), 7.59 (1H, m), 7.41 (1H, d, J=2.5 Hz), 7.35 (1H, dd, J=7.8, 7.8 Hz), 7.31 (1H, d, J=8.8 Hz), 7.25 (1H, dd, J=8.8, 2.5 Hz), 7.15–7.06 (2H, m), 6.98 (1H, d, J=7.8 Hz), 5.99 (2H, s), 5.37 (2H, s), 3.80 (3H, s).

IR (KBr) cm$^{-1}$: 3432, 1676, 1629, 1587, 1497, 1378, 1285, 1239, 1165, 1030, 829, 598.

Also, the second-deposited crystals were further purified through recrystallization (with DMF-ether), to thereby obtain 6-methoxy-3-{1-[3-(2-quinolylmethoxy)benzyl]tetrazolyl}quinolin-2-one (12.1 g, yield: 19.0%) as pale yellow powder.

mp: 215–217° C. (d.)

$^1$H-NMR (DMSO-d$_6$) δ (ppm): 12.39 (1H, br), 8.35 (1H, d, J=8.8 Hz), 8.31 (1H, s), 8.00 (1H, d, J=7.8 Hz), 7.98 (1H, d, J=7.3 Hz), 7.78 (1H, ddd, J=8.3, 6.8, 1.5 Hz), 7.62 (1H, dd, J=7.8, 7.3 Hz), 7.55 (1H, d, J=8.3 Hz), 7.38 (1H, d, J=8.8 Hz), 7.34–7.27 (2H, m), 7.20 (1H, m), 6.97–6.90 (2H, m), 6.77 (1H, d, J=7.8 Hz), 5.73 (2H, s), 5.23 (2H, s), 3.78 (3H, s).

IR (KBr) cm$^{-1}$: 3434, 1665, 1625, 1498, 1453, 1380, 1264, 1244, 1171, 1034, 827.

Examples 3 Through 34

In a manner similar to that of Examples 1 and 2, the compounds shown in Tables 3 and 4 below were obtained.

TABLE 3

| Ex. | Compound | m.p. |
| --- | --- | --- |
| 3 | 3-{1-{3-[N-(2-Ethoxyethyl)benzimidazol-2-ylmethoxy]benzyl}tetrazolyl}-6-hydroxyquinolin-2-one | 200~202° C. (d.) |
| 4 | 3-{1-{4-[N-(2-Ethoxyethyl)benzimidazol-2-ylmethoxy]benzyl}tetrazolyl}-6-hydroxyquinolin-2-one | 240~242° C. (d.) |
| 5 | 3-{2-{4-[N-(2-Ethoxyethyl)benzimidazol-2-ylmethoxy]benzyl}tetrazolyl}-6-hydroxyquinolin-2-one | 245~248° C. (d.) |
| 6 | 3-{2-{4-[N-(2-Ethoxyethyl)benzimidazol-2-ylmethoxy]benzyl}tetrazolyl}-6-methoxyquinolin-2-one | 200~202° C. (d.) |
| 7 | 3-{1-{4-[N-(2-Ethoxyethyl)benzimidazol-2-ylmethoxy]benzyl}tetrazolyl}-6-methoxyquinolin-2-one | 234~236° C. (d.) |
| 8 | 3-{2-[3-(N-Methylbenzimidazol-2-ylmethoxy)benzyl]tetrazolyl}quinolin-2-one | 262~265° C. (d.) |
| 9 | 3-{1-[3-(N-Methylbenzimidazol-2-ylmethoxy)benzyl]tetrazolyl}quinolin-2-one | 234~236° C. (d.) |

TABLE 3-continued

| Ex. | Compound | m.p. |
|---|---|---|
| 10 | 6-Methoxy-3-{2-[3-(2-quinazolylmethoxy)-benzyl]tetrazolyl}quinolin-2-one | 186~189° C. |
| 11 | 6-Methoxy-3-{2-[4-(2-quinazolylmethoxy)-benzyl]tetrazolyl}quinolin-2-one | 197~199° C. (d.) |
| 12 | 6-Methoxy-3-{1-[4-(2-quinazolylmethoxy)-benzyl]tetrazolyl}quinolin-2-one | 197~199° C. (d.) |
| 13 | 6-Methoxy-3-{2-[3-[2-(2-quinolyl)ethenyl]-benzyl}tetrazolyl}quinolin-2-one | 241~244° C. (d.) |
| 14 | 6-Methoxy-3-{1-{3-[2-(2-quinolyl)ethenyl]-benzyl}tetrazolyl}quinolin-2-one | 250~252° C. (d.) |
| 15 | 5-Ethoxy-8-methyl-3-{2-[3-(2-quinolylmethoxy)-benzyl]tetrazolyl}quinolin-2-one | 221~223° C. |
| 16 | 5-Ethoxy-8-methyl-3-{2-[4-(2-quinolylmethoxy)-benzyl]tetrazolyl}quinolin-2-one | 150~154° C. (d.) |
| 17 | 6-tert-Butyl-3-{2-[3-(2-quinolylmethoxy)-benzyl]tetrazolyl}quinolin-2-one | 102~105° C. |
| 18 | 6-tert-Butyl-3-{1-[3-(2-quinolylmethoxy)-benzyl]tetrazolyl}quinolin-2-one | 105~107° C. |

TABLE 4

| Ex. | Compound | m.p. |
|---|---|---|
| 19 | 6-tert-Butyl-3-{1-[4-(2-quinolylmethoxy)-benzyl]tetrazolyl}quinolin-2-one | 216~219° C. |
| 20 | 7-Hydroxy-3-{1-[3-(2-quinolylmethoxy)benzyl]-tetrazolyl}quinolin-2-one | 262~264° C. (d.) |
| 21 | 8-Hydroxy-3-{1-[3-(2-quinolylmethoxy)benzyl]-tetrazolyl}quinolin-2-one | 262~264° C. (d.) |
| 22 | 6-Hydroxy-3-{2-[4-(2-quinolylmethoxy)benzyl]-tetrazolyl}quinolin-2-one | 231~234° C. (d.) |
| 23 | 6-Hydroxy-3-{1-[4-(2-quinolylmethoxy)benzyl]-tetrazolyl}quinolin-2-one | 250~252° C. (d.) |
| 24 | 6-Methoxy-3-{2-[4-(2-quinolylmethoxy)benzyl]-tetrazolyl}quinolin-2-one | 206~210° C. (d.) |
| 25 | 6-Methoxy-3-{1-[4-(2-quinolylmethoxy)benzyl]-tetrazolyl}quinolin-2-one | 206~209° C. (d.) |
| 26 | 3-{2-[3-(2-Quinolylmethoxy)benzyl]-tetrazolyl}quinolin-2-one | 226~229° C. (d.) |
| 27 | 3-{1-[3-(2-Quinolylmethoxy)benzyl]-tetrazolyl}quinolin-2-one | 238~241° C. (d.) |
| 28 | 6-Hydroxy-3-{2-[3-(2-quinolylmethoxy)benzyl]-tetrazolyl}quinolin-2-one | 260~267° C. (d.) |
| 29 | 6-Hydroxy-3-{1-[3-(2-quinolylmethoxy)benzyl]-tetrazolyl}quinolin-2-one | 272~275° C. (d.) |
| 30 | 6-[3-(2-Quinolylmethoxy)benzyl]oxy-3-{2-[3-(2-quinolylmethoxy)benzyl]tetrazolyl}quinolin-2-one | 195~199° C. (d.) |
| 31 | 1-[3-(2-Quinolylmethoxy)benzyl]-3-{2-[3-(2-quinolylmethoxy)benzyl]tetrazolyl}quinolin-2-one | 114~116° C. |
| 32 | 6-Hydroxy-1-[3-(2-quinolylmethoxy)benzyl]-3-{2-[3-(2-quinolylmethoxy)benzyl]tetrazolyl}quinolin-2-one | 175~178° C. (d.) |
| 33 | 6-tert-Butyl-1-[3-(2-quinolylmethoxy)benzyl]-3-{1-[3-(2-quinolylmethoxy)benzyl]tetrazolyl}quinolin-2-one | 96~99° C. |
| 34 | 6-Methoxy-1-[4-(N-methylbenzimidazole-2-ylmethoxy)benzyl]-3-{2-[4-N-methylbenzimidazol-2-ylmethoxy)benzyl]tetrazolyl}quinolin-2-one | 217~219° C. |

Examples 35 and 36

Synthesis of 6-methoxymethoxy-3-{2-[3-(2-quinolylmethoxy)benzyl]tetrazolyl}quinolin-2-one and 6-methoxymethoxy-3-{1-[3-(2-quinolylmethoxy)benzyl]tetrazolyl}quinolin-2-one In a manner similar t that of Examples 1 and 2, the title compounds were obtained.

The data of 6-methoxymethoxy-3-{2-[3-(2-quinolylmethoxy)benzyl]tetrazolyl}quinolin-2-one are as follows:

mp: 197–200° C. (d.)

$^1$H-NMR (CDCl$_3$) δ (ppm): 11.24 (1H, br), 8.63 (1H, s), 8.18 (1H, d, J=8.3 Hz), 8.09 (1H, d, J=8.5 Hz), 7.72 (1H, ddd, J=8.5, 7.1, 1.5 Hz), 7.64 (1H, d, J=8.5 Hz), 7.52 (1H, ddd, J=8.1, 6.8, 1.2 Hz), 7.35–7.24 (4H, m), 7.13 (1H, m), 7.10–6.99 (2H, m), 5.87 (2H, s), 5.39 (2H, s), 5.20 (2H, s), 3.50 (3H, s).

IR (KBr) cm$^{-1}$: 1667, 1623, 1588, 1510, 1493, 1443, 1428, 1289, 1230, 1155, 1074, 996, 825, 529.

The data of 6-methoxymethoxy-3-{1-[3-(2-quinolylmethoxy)benzyl]tetrazolyl}quinolin-2-one are as follows:

mp: 202–206° C. (d.)

$^1$H-NMR (CDCl$_3$) δ (ppm): 11.60 (1H, br), 8.13 (1H, s), 8.12 (1H, d, J=8.8 Hz), 8.05 (1H, d, J=8.4 Hz), 7.82 (1H, d, J=7.0 Hz), 7.73 (1H, dd, J=8.1, 7.0 Hz), 7.59–7.49 (2H, m), 7.34–7.19 (3H, m), 7.16 (1H, dd, J=8.7, 8.7 Hz), 5.86 (2H, s), 5.37 (2H, s), 5.21 (2H, s), 3.47 (3H, s).

IR (KBr) cm$^{-1}$: 1664, 1623, 1600, 1497, 1291, 1266, 1158, 1001, 983, 825, 781, 750.

Example 37
(Alternative Synthesis Method for Obtaining the Compound of Example 28)

Synthesis of 6-hydroxy-3-{2-[3-(2-quinolylmethoxy)benzyl]tetrazolyl}quinolin-2-one 6-methoxymethoxy-3-{2-[3-(2-quinolylmethoxy)-benzyl]tetrazolyl}quinolin-2-one (444 mg, 0.85 mmol) was dissolved in a mixture (100 ml) of chloroform-methanol (10:1). A solution (5 ml) of hydrochloric acid (4N) in ethyl acetate was added to the resultant mixture, and the mixture was stirred at room temperature for 17 hours. Water (400 ml) was added thereto, and a saturated aqueous solution of sodium hydrogencarbonate was added dropwise so as to neutralize the aqueous phase, followed by extraction with a mixture of chloroform-methanol (10:1). The organic phase was dried over magnesium sulfate anhydrate, and the solvent was removed under reduced pressure. The residue was recrystallized from a chloroform-methanol-diethylether mixture, to thereby obtain the title compound as yellow leaf crystals (353 mg, 0.74 mmol, 87.2%).

mp: 260–267° C. (d.)

$^1$H-NMR (CDCl$_3$-CD$_3$OD) δ (ppm): 8.53 (1H, s), 8.35 (1H, d, J=8.6 Hz), 8.06 (1H, d, J=8.3 Hz), 7.89 (1H, d, J=8.3 Hz), 7.78 (1H, ddd, J=8.6, 7.1, 1.5 Hz), 7.72 (1H, d, J=8.6 Hz), 7.60 (1H, m), 7.33 (1H, dd, J=8.8, 8.1 Hz), 7.27 (1H, d, J=8.8 Hz), 7.18 (1H, dd, J=8.8, 2.8 Hz), 7.15–7.02 (4H, m), 5.88 (2H, s), 5.39 (2H, s).

IR (KBr) cm$^{-1}$: 1661, 1614, 1508, 1429, 1287, 1229, 1160, 1029, 826, 781.

Example 38

Synthesis of 6-methoxy-1-methyl-3-{2-[3-(2-quinolylmethoxy)benzyl]tetrazolyl}quinolin-2-one To a mixture of 6-methoxy-3-{2-[3-(2-quinolylmethoxy)benzyl]tetrazolyl}quinolin-2-one (1.61 g, 3.30 mmol) and potassium carbonate (684 mg, 4.95 mmol), was added DMF (30 ml). Methyl iodinate (562 mg, 3.96 mmol) was added dropwise to the resultant mixture, and thereafter stirred for four hours at a bath temperature of 80° C. The solvent of the reaction mixture was removed under reduced pressure. Water was added to the mixture, and the organic phase was extracted therefrom with a mixture of chloroform-methanol (10:1). The organic phase was dried over sodium sulfate anhydrate, subjected to silica gel column chromatography (with chloroform-methanol (50:1)), and concentrated under reduced pressure. The resultant residue was recrystallized from a chloroform-n-hexan-ether mixture, to thereby obtain the title compound (1.35 g, 2.68 mmol, 81.1%) as pale yellow powder.

mp: 125–127°

$^1$H-NMR (CDCl$_3$) δ (ppm): 8.57 (1H, s), 8.19 (1H, d, J=8.6 Hz), 8.07 (1H, d, J=8.5 Hz), 7.81 (1H, d, J=8.3 Hz), 7.72 (1H, ddd, J=8.3, 6.8, 1.5 Hz), 7.64 (1H, d, J=8.6 Hz), 7.53 (1H, dd, J=8.3, 7.8 Hz), 7.36 (1H, d, J=9.0 Hz), 7.32–7.24 (2H, m), 7.13–7.09 (2H, m), 7.04 (1H, d, J=7.6 Hz), 6.99 (1H, dd, J=7.6, 2.2 Hz), 5.85 (2H, s), 5.36 (2H, s), 3.89 (3H, s), 3.81 (3H, s).

IR (KBr) cm$^{-1}$: 3442, 1664, 1589, 1577, 1442, 1237, 1160, 1066, 1031, 928, 786, 768.

Examples 39 Through 43

In a manner similar to that of Example 38, the compounds shown in Table 5 below were obtained.

TABLE 5

| Ex. | Compound | m.p. |
| --- | --- | --- |
| 39 | 1-Dimethylaminoethyl-6-hydroxy-3-{2-[3-(2-quinolylmethoxy)benzyl]tetrazolyl}quinolin-2-one | 179~181° C. (d.) |
| 40 | 1-Dimethylaminoethyl-6-hydroxy-3-{1-[3-(2-quinolylmethoxy)benzyl]tetrazolyl}quinolin-2-one | 153~155° C. |
| 41 | 1-Dimethylaminoethyl-6-methoxy-3-{2-[3-(2-quinolylmethoxy)benzyl]tetrazolyl}quinolin-2-one | 154~158° C. |
| 42 | 1-Dimethylaminopropyl-6-hydroxy-3-{2-[3-(2-quinolylmethoxy)benzyl]tetrazolyl}quinolin-2-one | 169~172° C. (d.) |
| 43 | 1-Dimethylaminoethyl-6-hydroxy-3-{2-[3-(2-quinolylethenyl)benzyl]tetrazolyl}quinolin-2-one | 148~152° C. (d.) |

Example 44

Synthesis of 1-(3-chloropropyl)-6-methoxy-3-{2-[3-(2-quinolylmethoxy)benzyl]tetrazolyl}quinolin-2-one A mixture of 6-methoxy-3-{2-[3-(2-quinolylmethoxy)benzyl]tetrazolyl}quinolin-2-one (1.00 g, 2.04 mmol), potassium, carbonate (564 mg, 4.08 mmol), 1-bromo-3-chloropropane (962 mg, 6.12 mmol), and DMF (100 ml) was stirred for four hours at a bath temperature of 60° C. The solvent of the reaction mixture was removed under reduced pressure. Water was then added to the mixture, and the mixture was extracted with chloroform-methanol (10:1). The thus-obtained organic phase was dried over magnesium sulfate anhydrate, and the solvent was removed under reduced pressure. The organic phase was then subjected to silica gel column chromatography (developer: chloroform-methanol (100:1)), purified, and crystallized from a chloroform-diethylether mixture, to thereby obtain the title compound (546 mg, 0.963 mmol, 47.2%) as pale yellow powder.

mp: 150–152° C.

$^1$H-NMR (CDCl$_3$) δ (ppm): 8.60 (1H, s), 8.18 (1H, d, J=8.5 Hz), 8.07 (1H, d, J=8.3 Hz), 7.81 (1H, d, J=9.0 Hz), 7.72 (1H, ddd, J=8.3, 7.8, 1.5 Hz), 7.64 (1H, d, J=8.3 Hz), 7.53 (1H, dd, J=8.1, 6.8 Hz), 7.46 (1H, d, J=9.3 Hz), 7.33–7.24 (2H, m), 7.15–7.08 (2H, m), 7.06–6.96 (2H, m), 5.85 (2H, s), 5.36 (2H, s), 4.53 (2H, t, J=7.8 Hz), 3.89 (3H, s), 3.73 (2H, t, J=6.3 Hz), 2.29 (2H, m).

IR (KBr) cm$^{-1}$: 1660, 1590, 1573, 1508, 1445, 1428, 1267, 1159, 829, 767.

Further, the by-product was crystallized from a chloroform-diethylether mixture, to thereby obtain 2-chloropropoxy-6-methoxy-3-{2-[3-(2-quinolylmethoxy)benzyl]tetrazolyl}quinoline (173 mg, 0.305 mmol, 15.0%) as white powder.

Example 45

Synthesis of 1-{3-[4-(2-quinolylmethyl)-1-piperazinyl]propyl}-6-methoxy-3-(2-[3-(2-quinolylmethoxy)benzyl]tetrazolyl)quinolin-2-one dihydrochloride A mixture of 1-(3-chloropropyl)-6-methoxy-3-{2-[3-(2-quinolylmethoxy)benzyl]tetrazolyl}quinolin-2-one (179 mg, 0.316 mmol) and N-(2-quinolylmethyl)piperazine (287 mg, 1.26 mmol) was stirred under an argon flow at 120° C. for 2.5 hours. The mixture was allowed to cool, subjected to silica gel column chromatography (developer: chloroform-methanol (40:1)), and purified. Fractions including the target compound were collected, and concentrated under reduced pressure, to thereby obtain the free base of the title compound (219 mg, 0.289 mmol) as yellow oily matter. The thus-obtained free base of the title compound was dissolved in methanol (50 ml), and a solution of hydrochloric acid (4N) in ethyl acetate (144 μl, 0.576 mmol) was added to the resultant mixture. The mixture was crystallized from a methanol-diethylether mixture, to thereby obtain the title compound (184 mg, 0.22 mmol, 70.1%) as yellow powder.

mp: 182–186°

$^1$H-NMR (CDCl$_3$-CD$_3$OD) δ (ppm): 8.73 (1H, d, J=8.6 Hz), 8.66 (1H, d, J=8.1 Hz), 8.60 (1H, s), 8.53 (1H, d, J=8.1 Hz), 8.05–7.79 (6H, m), 7.70 (1H, dd, J=7.8, 7.3 Hz), 7.59 (1H, d, J=9.3 Hz), 7.40–7.30 (2H, m), 7.22–7.15 (2H, m), 7.10–7.04 (2H, m), 5.88 (2H, s), 5.55 (2H, s), 4.53 (2H, t, J=6.3 Hz), 4.34 (2H, s), 3.91 (3H, s), 3.54 (4H, br), 3.37 (2H, m), 3.22 (4H, br), 2.37 (2H, m).

IR (KBr) cm$^{-1}$: 1652, 1625, 1576, 1509, 1455, 1240, 1028, 772, 475.

Examples 46 Through 49

In a manner similar to that of Example 45, the compounds shown in Table 6 below were obtained.

TABLE 6

| Ex. | Compound | m.p. |
| --- | --- | --- |
| 46 | 6-Methoxy-1-[3-(4-methylpiperazinyl)propyl]-3-{2-[3-(2-quinolylmethoxy)benzyl]tetrazolyl}quinolin-2-one | 191~195° C. (d.) |
| 47 | 6-Methoxy-1-{4-[4-(2-quinolylmethyl)-piperazinyl]butyl}-3-{2-[3-(2-quinolylmethoxy)benzyl]tetrazolyl}quinolin-2-one dimalate | 179~181° C. (d.) |
| 48 | 6-Methoxy-1-{3-[4-(2-pyridylmethyl)-piperazinyl]propyl}-3-{2-[3-(2-quinolylmethoxy)benzyl]tetrazolyl}quinolin-2-one dihydrochloride | 161~164° C. (d.) |
| 49 | 6-Methoxy-3-{2-[3-(2-quinolylethenyl)benzyl]-tetrazolyl}-1-{3-[4-(2-quinolylmethyl)-piperazinyl]propyl}quinolin-2-one dimalate | 156~158° C. (d.) |

Example 50

Synthesis of 6-dimethylaminoethoxy-1-dimethylaminoethyl-3-{2-[3-(2-quinolylmethoxy)benzyl]tetrazolyl}quinolin-2-one dioxalate To a mixture of 6-dimethylaminoethyl-3-1-hydroxy-{1-[3-(2-quinolylmethoxy)benzyl]tetrazolyl}quinolin-2-one (700 mg, 1.28 mmol) and potassium carbonate (706 mg, 5.11 mmol), was added DMF (40 ml), and the resultant mixture was stirred. Dimethylaminoethylchloride (369 mg, 2.56 mmol) was then added to the mixture, and the mixture was stirred for three days at a bath temperature of 80° C.

The reaction mixture was concentrated under reduced pressure. After addition of water, the reaction mixture was extracted with a mixture of chloroform-methanol (10:1). The thus-obtained organic phase was dried over sodium sulfate anhydrate, and the solvent was removed under reduced pressure. The organic phase was then subjected to silica gel column chromatography (with chloroform-ammonia-saturated-methanol (10:1)). The solvent of the fractions including the target compound was removed under reduced pressure, to thereby obtain the free base of the title compound (254 mg, 0.411 mmol, 32.1%) as brown oily matter.

$^1$H-NMR (CDCl$_3$) δ (ppm): 8.57 (1H, s), 8.18 (1H, d, J=8.5 Hz), 8.06 (1H, d, J=8.3 Hz), 7.81 (1H, d, J=8.1 Hz), 7.73 (1H, ddd, J=8.5, 6.8, 1.5 Hz), 7.64 (1H, d, J=8.3 Hz), 7.52 (1H, dd, J=8.2, 6.8 Hz), 7.40 (1H, d, J=9.3 Hz), 7.34–7.23 (2H, m), 7.14 (1H, d, J=2.7 Hz), 7.10 (1H, s), 7.05–6.95 (2H, m), 5.86 (2H, s), 5.36 (2H, s), 4.50 (2H, t, J=8.1 Hz), 4.13 (2H, t, J=5.6 Hz), 2.77 (2H, t, J=5.6 Hz), 2.67 (2H, t, J=8.1Hz), 2.40 (6H, s), 2.36 (6H, s).

The thus-obtained free base of the title compound was dissolved in methanol, and oxalic acid (148 mg, 0.422 mmol) was added to the resultant mixture. Subsequently, the mixture was recrystallized from an acetone-ether mixture, to thereby obtain the dioxalate (211 mg, 0.270 mmol, 21.1%) of the title compound as brown powder.

mp: 172–176° C. (d.)

$^1$H-NMR (CDCl$_3$) δ (ppm): 8.52 (1H, s), 8.24 (1H, d, J=8.1 Hz), 8.05 (1H, d, J=8.6 Hz), 7.84 (1H, d, J=7.6 Hz), 7.78–7.67 (2H, m), 7.66 (1H, d, J=8.5 Hz), 7.56 (1H, ddd, J=9.3, 8.1, 1.2 Hz), 7.47–7.38 (1H, m), 7.31 (1H, dd, J=7.8, 8.1 Hz), 7.17 (1H, m), 7.12 (1H, m), 7.07–7.68 (2H, m), 5.85 (2H, s), 5.35 (2H, s), 4.70 (2H, m), 4.40 (2H, m), 3.49 (2H, m), 3.30 (2H, m), 2.95 (6H, s), 2.94 (6H, s).

IR (KBr) cm$^{-1}$: 3419, 1652, 1599, 1509, 1448, 1312, 1281, 1239, 1161, 1055, 831.

Example 51

Synthesis of 6-(3-chloropropyl)oxy-1-methyl-3-{2-[3-(2-quinolylmethoxy)benzyl]tetrazolyl}quinolin-2-one To a mixture of 6-hydroxy-1-methyl-3-{2-[3-(2-quinolylmethoxy)benzyl]tetrazolyl}quinolin-2-one (600 mg, 1.22 mmol) and potassium carbonate (337 mg, 2.44 mmol), was added DMF (100 ml), and the resultant mixture was stirred. 1-Bromo-3-chloropropane (578 mg, 3.64 mmol) was then added thereto, followed by stirring at a bath temperature of 60° C. for four hours. The reaction mixture was concentrated under reduced pressure, and water was added thereto, followed by extraction with a mixture of chloroform-methanol (10:1). The residue was dried over sodium sulfate anhydrate, and the solvent was removed under reduced pressure, to thereby obtain the title compound (638 mg) in a crude form as yellow oily matter.

$^1$H-NMR (CDCl$_3$) δ (ppm): 8.52 (1H, s), 8.17 (1H, d, J=8.6 Hz), 8.06 (1H, d, J=8.5 Hz), 7.80 (1H, d, J=8.1 Hz), 7.71 (1H, ddd, J=8.3, 7.1, 1.5 Hz), 7.63 (1H, d, J=8.5 Hz), 7.51 (1H, dd, J=8.1, 6.8 Hz), 7.35–7.21 (3H, m), 7.14–7.09 (2H, m), 7.04 (1H, d, J=7.6 Hz), 6.98 (1H, dd, J=8.3, 2.4 Hz), 5.85 (2H, s), 5.35 (2H, s), 4.17 (2H, t, J=5.9 Hz), 3.84–3.73 (5H, m), 2.27 (2H, t,J=6.1 Hz).

Example 52

Synthesis of 1-methyl-6-[3-(4-metylpiperazinyl)propyl]oxy-3-{2-[3-(2-quinolylmethoxy)benzyl]tetrazolyl}quinolin-2-one trihydrochloride A mixture of crude 6-[3-chloropropyl]oxy-1-methyl-3-{2-[3-(2-quinolylmethoxy)benzyl]tetrazolyl}quinolin-2-one (180 mg, 0.317 mmol) and N-methylpiperazine (127 mg, 1.27 mmol) was stirred under an argon flow at a bath temperature of 120° C. for 90 minutes. The reaction mixture was concentrated under reduced pressure, and purified through silica gel chromatography (developer: chloroform-methanol (20:1)). Fractions containing the target compound were collected, and concentrated under reduced pressure, to thereby obtain the free base of the title compound (180 mg, 0.285 mmol) as yellow oily matter. The thus-obtained free base was dissolved in methanol (2 ml), and a solution of hydrochloric acid (4N) in ethyl acetate (285 μl, 1.14 mmol) was added thereto. The mixture was crystallized from a methanol-diethylether mixture, to thereby obtain the trihydrochloride; i.e., the title compound, as yellow needles (143 mg, 0.203 mmol, 64.1%).

mp: 188–192° C. (d.)

$^1$H-NMR (CDCl$_3$-CD$_3$OD) δ (ppm): 8.77 (1H, d, J=8.6 Hz), 8.54 (1H, s), 8.46 (1H, d, J=8.8 Hz), 8.11 (1H, d, J=8.6 Hz), 8.08–7.98 (2H, m), 7.82 (1H, dd, J=7.6, 7.3 Hz), 7.46–7.32 (2H, m), 7.30–7.05 (5H, m), 5.90 (2H, s), 5.69 (2H, s), 4.21 (2H, overlapped with solvent), 3.90–3.65 (11H, m), 3.51 (2H, m), 2.98 (3H, m), 2.41 (2H, br).

IR (KBr) cm$^{-1}$: 1647, 1623, 1578, 1510, 1456, 1384, 1241, 1162, 1060, 963.

Example 53

Synthesis of 6-{3-[4-(2-quinolylmethyl)piperazinyl]propyl}oxy-1-methyl-3-{2-[3-(2-quinolylmethoxy)benzyl]tetrazolyl}quinolin-2-one In a manner similar to that of Example 52, the title compound was obtained.

mp: 174–178° C. (d.)

$^1$H-NMR(DMSO-d$_3$) δ (ppm): 8.62 (1H, d, J=8.3 Hz), 8.53 (1H, s), 8.48 (1H, d, J=8.8 Hz), 8.21–7.97 (4H, m), 7.93–7.71 (5H, m), 7.66–7.50 (3H, m), 7.41–7.33 (2H, m), 7.16–7.07 (2H, m), 7.01 (1H, d, J=7.8 Hz), 6.00 (2H, s), 5.42 (2H, s), 4.60 (2H, br), 4.17 (2H, t, J=6.1 Hz), 3.80–3.30 (8H, overlapped with solvent), 3.69 (3H, s), 2.25 (2H, br).

IR (KBr) cm$^{-1}$: 1647, 1600, 1578, 1509, 1449, 1430, 1239, 1159.

Example 54

Synthesis of 6-butyryloxy-3-{2-[3-(2-quinolylmethoxy)benzyl]tetrazolyl}quinolin-2-one 6-Hydroxy-3-{2-[3-(quinolyln-2-ylmethoxy)benzyl]tetrazolyl}quinolin-2-one (250 mg, 0.522 mmol) was dissolved in pyridine (30 ml), and butyric anhydride (172 μl, 1.05 mmol) was added thereto, followed by stirring at room temperature for 20 hours. A small amount of methanol was added to the reaction mixture, and the solvent was then removed. The residue was dissolved in a chloroform-methanol (10:1) mixture, followed by sequential washing with hydrochloric acid (2N), water, a saturated aqueous solution of sodium hydrogencarbonate, and water. The organic phase was dried over magnesium sulfate anhydrate, and the solvent was removed under reduced pressure. The residue was purified through silica gel chromatography (developer: chloroform-methanol (10:1)), followed by recrystallization with a chloroform-methanol-diethylether mixture, to thereby obtain the title compound as white powder (265 mg, 0.485 mmol, 92.8%).

mp: 200–202° C. (d.)

$^1$H-NMR (CDCl$_3$) δ (ppm): 11.1 (1H, br), 8.64 (1H, s), 8.16 (1H, d, J=8.8 Hz), 8.05 (1H, d, J=8.1Hz), 7.79 (1H, d, J=8.1 Hz), 7.70 (1H, ddd, J=8.4, 7.0, 1.5 Hz), 7.62 (1H, d, J=8.4 Hz), 7.51 (1H, m), 7.42 (1H, d, J=2.2 Hz), 7.36–7.27 (3H, m), 7.14–6.98 (3H, m), 5.87(2H, s), 5.37(2H, s), 2.67(2H, t, J=7.3 Hz), 1.80(2H, tq, J=7.3, 7.3 Hz), 1.06 (3H, t, J=7.3 Hz).

IR (KBr) cm$^{-1}$: 1755, 1675, 1586, 1497, 1453, 1226, 1156, 1030, 828, 757.

Examples 55 Through 64

In a manner similar to that of Example 54, the following compounds were obtained.

TABLE 7

| Ex. | Compound | m.p. |
| --- | --- | --- |
| 55 | 6-Butyryloxy-3-{1-[3-(2-quinolylmethoxy)benzyl]-tetrazolyl}quinolin-2-one | 189~191° C. (d.) |
| 56 | 6-Acetoxy-3-{2-[4-(2-quinolylmethoxy)benzyl]-tetrazolyl}quinolin-2-one | 226~228° C. (d.) |
| 57 | 6-Acetoxy-3-{1-[4-(2-quinolylmethoxy)benzyl]-tetrazolyl}quinolin-2-one | 235~238° C. (d.) |
| 58 | 6-Acetoxy-3-{2-[3-(2-quinolylmethoxy)benzyl]-tetrazolyl}quinolin-2-one | 222~225° C. (d.) |
| 59 | 6-Acetoxy-3-{1-[3-(2-quinolylmethoxy)benzyl]-tetrazolyl}quinolin-2-one | 218~221° C. (d.) |
| 60 | 6-Propionyloxy-3-{2-[3-(2-quinolylmethoxy)-benzyl]tetrazolyl}quinolin-2-one | 216~218° C. (d.) |
| 61 | 6-Propionyloxy-3-{1-[3-(2-quinolylmethoxy)-benzyl]tetrazolyl}quinolin-2-one | 201~203° C. (d.) |
| 62 | 6-Isobutyryloxy-3-{2-[3-(2-quinolylmethoxy)benzyl]tetrazolyl}quinolin-2-one | 195~197° C. (d.) |
| 63 | 6-Isobutyryloxy-3-{1-[3-(2-quinolylmethoxy)-benzyl]tetrazolyl}quinolin-2-one | 196~199° C. (d.) |
| 64 | 6-Glycyloxy-3-{2-[3-(2-quinolylmethoxy)-benzyl]tetrazolyl}quinolin-2-one | 196~200° C. (d.) |

Test Example 1

Antihistaminic Action and Antileukotriene Action (in vitro Test)

A guinea pig was subjected to ileectomy, and the ileum was cut to lengths of about 2 cm. Each piece of ileum was suspended in a Tyrode's buffer placed in a 20-ml organ bath. Isotonic contraction in response to histamine or leukotriene D$_4$ as recorded by use of a recording apparatus. The Tyrode's buffer was aerated with a gas mixture (95% O$_2$–5% CO$_2$) while the temperature of the buffer was maintained at 29° C. Antihstaminic activity was tested by adding 10$^{-8}$ to 10$^{-4}$ M histamine to the organ bath and obtaining a dose-response curve. After washing with a buffer several times, a test compound was added to the organ bath. Thirty minutes later, another dose-response curve of histamine was obtained. For the test of antileukotriene activity, there were investigated effects exerted by addition of a 10$^{-5}$ M test compound on the contraction induced with 10$^{-8}$ M LTD$_4$. In Table 8, antihistaminic action is indicated by pA$_2$ or pD'$_2$, whereas antileukotriene action is indicated by IC$_{50}$.

TABLE 8

| Example | Anti-histaminic action | Anti-LTD$_4$ action IC$_{50}$(M) |
| --- | --- | --- |
| 1 | 5.53 pD'$_2$ | 9.0 × 10$^{-8}$ |
| 2 | 5.38 pA$_2$ | 2.5 × 10$^{-7}$ |
| 6 | 7.39 pA$_2$ | 1.1 × 10$^{-6}$ |
| 26 | 5.24 pD'$_2$ | 1.79 × 10$^{-7}$ |
| 38 | 5.52 pD'$_2$ | 1.6 × 10$^{-7}$ |
| 39 | 7.52 pA$_2$ | 5.0 × 10$^{-7}$ |
| 40 | 6.60 pA$_2$ | 6.4 × 10$^{-7}$ |
| 41 | 5.58 pD'$_2$ | 5.9 × 10$^{-7}$ |
| 42 | 7.26 pA$_2$ | 8.4 × 10$^{-7}$ |
| 43 | 6.76 pA$_2$ | 3.6 × 10$^{-6}$ |
| 45 | 7.66 pA$_2$ | 6.4 × 10$^{-7}$ |
| 47 | 7.70 pA$_2$ | 2.1 × 10$^{-6}$ |
| 48 | 6.94 pA$_2$ | 5.0 × 10$^{-7}$ |
| 52 | 6.04 pA$_2$ | 1.3 × 10$^{-6}$ |

Test Example 2

H$_1$ Receptor Binding Inhibitory Test 50 mM phosphate buffer (pH 7.5, 1 ml) containing 0.5 nM [$^3$H] mepyramine (activity: 22 Ci/mmol), guinea pig cerebral membrane protein, and a test compound was incubated at 37° C. for 30 minutes. Reaction was stopped by addition of ice-cold phosphate buffer, and immediately thereafter, the reaction mixture was filtered by use of a Wattman CF/C filter. The filter was washed twice, each time with 20 ml ice-cold buffer. Radioactivity of the residue was measured by use of a liquid scintillation counter. From the value as obtained when a test compound was not added and values as obtained when the test compound was added at different concentrations, there was determined a dose-response curve representing suppression action of the test compound, from which a 50% inhibitory concentration (IC$_{50}$) was obtained. Based on the IC$_{50}$ value and by use of the Cheng-Prusoff equation, a dissociation constant (K$_D$) was calculated (Table 9). In a saturation test, 10$^{-4}$ M R(−)-dimetindene was used for the measurement of the amount of non-specific binding. From the saturation test, it was found that a single type of receptor was involved, and the saturation amount of binding (Bmax) was 278±24 fmol/mg protein. Also, the dissociation constant (K$_D$) of [$^3$H]mepyramine was 3.30±0.26×10$^{-9}$ M, and the slope as analyzed in accordance with Hill plots was 1.005. The figures in Table 9 represent dissociation constants K$_D$ (M) or inhibition (%) at a high concentration (a: 100 μM, b: 10 μM).

Test Example 3

LTD$_4$ Receptor Binding Inhibitory Test 10 mM Piperazine N,N'-bis(2-ethane sulfonate) buffer (pH 7.5, 0.3 ml) containing 0.2 nM [$^3$H] leukotriene D$_4$, guinea pig lung protein, and a test compound was incubated at 22° C. for 30 minutes. Reaction was stopped by addition of ice-cold Tris-HCl/NaCl (10 mM/100 mM, pH 7.5) buffer, and immediately thereafter, the reaction mixture was filtered by use of a Wattman CF/C filter. The filter was washed twice, each time with 20 ml ice-cold buffer. Radioactivity of the residue was measured by use of a liquid scintillation counter. In a manner similar to that applied to the case of the H$_1$ receptor, IC$_{50}$ and the dissociation constant (K$_D$) of the test compound were obtained (see Table 9). In a saturation test, 2 μM leukotriene D$_4$ was used for the measurement of the amount of non-specific binding. From the saturation test, it was found that there was involved a single type of receptor, and the saturation amount of binding (Bmax) was 988 fmol/mg protein. Also, the dissociation constant (K$_D$) of

[³H]leukotriene $D_4$ was $2.16 \times 10^{-10}$ M, and the slope as analyzed in accordance with Hill plots was 0.99.

TABLE 9

| Example | $H_1$ Receptor $K_D(M)$ | $LTD_4$ Receptor $K_D(M)$ |
|---------|------------------------|---------------------------|
| 1  | $2.96 \times 10^{-6}$ | $1.14 \times 10^{-7}$ |
| 6  | $3.29 \times 10^{-6}$ | $8.11 \times 10^{-6}$ |
| 8  | $9.38 \times 10^{-6}$ | $1.43 \times 10^{-7}$ |
| 9  | $1.37 \times 10^{-5}$ | $3.20 \times 10^{-7}$ |
| 18 | $2.28 \times 10^{-5}$ | $5.09 \times 10^{-7}$ |
| 22 | $3.01 \times 10^{-5}$ | $3.64 \times 10^{-7}$ |
| 24 | $9.51 \times 10^{-6}$ | $2.05 \times 10^{-7}$ |
| 25 | $1.39 \times 10^{-5}$ | $5.86 \times 10^{-9}$ |
| 26 | $8.95 \times 10^{-5}$ | $1.79 \times 10^{-7}$ |
| 28 | $1.39 \times 10^{-5}$ | $2.10 \times 10^{-8}$ |
| 29 | $5.72 \times 10^{-5}$ | $1.36 \times 10^{-8}$ |
| 56 | $8.47 \times 10^{-5}$ | $3.36 \times 10^{-7}$ |
| 58 | $4.80 \times 10^{-4}$ | $3.82 \times 10^{-8}$ |
| 64 | $6.19 \times 10^{-5}$ | $2.21 \times 10^{-8}$ |

As described above, the tetrazole derivative or a salt thereof according to the present invention is endowed with excellent antileukotriene activity and anti-histaminic activity and thus is useful as a medicine for the prevention and treatment of asthma.

What is claimed is:

1. A tetrazole derivative, or a salt thereof, represented by formula (1): wherein

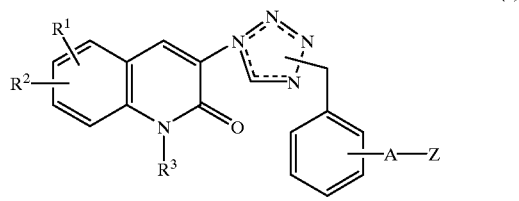

(1)

$R^1$ and $R^2$, independently, represent a hydrogen atom, a hydroxyl group, a lower alkyl group, an alkoxy group having 1 to 6 carbon atoms, an alkoxy group having 1 to 6 carbon atoms substituted with an alkoxy group having 1 to 6 carbon atoms, a halogen atom, a phenyl group, or a di-(C1–C4)alkylamino group; an alkanoyloxy group having 2 to 5 carbon atoms; or an alkanoyloxy group having 2 to 5 carbon atoms substituted with an amino group;

$R^3$ represents a hydrogen atom, a lower alkyl group, or a lower alkyl group substituted with a halogen atom, an amino group, a phenyl group, or a phenyl group substituted with a C1–C4 alkyl group;

A represents a methyleneoxy group or a vinylene group;

Z represents an unsubstituted benzimidazole or a benzimidazole group substituted with a C1–C4alkyl group or a (C1–C4)alkoxy(C1–C4)alkyl group;

and a broken line indicates that there may be a double bond.

2. The tetrazole derivative or a salt thereof as defined in claim 1, wherein Z represents a benzimidazole group substituted with a C1–C4 alkyl group or a (C1–C4)alkoxy (C1–C4)alkyl group.

3. The tetrazole derivative or a salt thereof as defined in claim 1, wherein Z represents an unsubstituted benzimidazole group.

4. The tetrazole derivative or a salt thereof as defined in claim 1, wherein said lower alkyl group has 1 to 6 carbon atoms.

5. The tetrazole derivative or a salt thereof as defined in claim 1, wherein $R^3$ is a hydrogen atom, a methyl group, or a dimethylaminomethyl group.

6. The tetrazole derivative or a salt thereof as defined in claim 1, which is an addition salt of a mineral acid or an inorganic acid.

7. The addition salt of the tetrazole derivative as defined in claim 6, which is selected from the group consisting of hydrochlorides, hydrobromides, hydroiodides, sulfates, phosphates, benzoates, methanesulfonates, ethanesulfonates, benzenesulfonates, p-toluenesulfonates, oxalates, maleates, fumarates, tartarates, and citrates.

8. The tetrazole derivative or a salt thereof as defined in claim 1, which is 3-{1-{3-[N-(2-Ethoxyethyl)benzimidazol-2-ylmethoxy]benzyl}tetrazolyl}-6-hydroxyquinolin-2-one, 3-{1-{4-[N-(2-Ethoxyethyl)benzimidazol-2-ylmethoxy]benzyl}tetrazolyl}-6-hydroxyquinolin-2-one, 3-{2-{4-[N-(2-Ethoxyethyl)benzimidazol-2-ylmethoxy]benzyl}tetrazolyl}-6-hydroxyquinolin-2-one, 3-{2-{4-[N-(2-Ethoxyethyl)benzimidazol-2-ylmethoxy]benzyl}tetrazolyl}-6-hydroxyquinolin-2-one, 3-{1-{4-[N-(2-Ethoxyethyl)benzimidazol-2-ylmethoxy]benzyl}tetrazolyl}-6-hydroxyquinolin-2-one, 3-{2-[3-(N-Methylbenzimidazol-2-ylmethoxy)benzyl]tetrazolyl}quinolin-2-one or 3-{1-[3-(N-Methylbenzimidazol-2-ylmethoxy)benzyl]tetrazolyl}quinolin-2-one.

9. A composition, comprising the tetrazole derivative or a salt thereof as defined in claim 1, and a pharmaceutically acceptable carrier.

10. The composition of claim 9, which is in the form of a tablet, capsule, granule, powder, syrup or suppository.

11. A method of treating asthma, which method comprises administering to a patient in need thereof an effective amount of a tetrazole derivative or a salt thereof as described in claim 1.

* * * * *

UNITED STATES PATENT AND TRADEMARK OFFICE
CERTIFICATE OF CORRECTION

PATENT NO.    : 6,117,886                                Page 1 of 2
DATED         : September 12, 2000
INVENTOR(S)   : Hendrik Timmerman et al.

It is certified that error appears in the above-identified patent and that said Letters Patent is hereby corrected as shown below:

Title page,
Item [57], ABSTRACT,

"
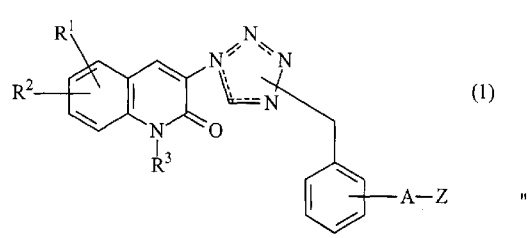

should read

--
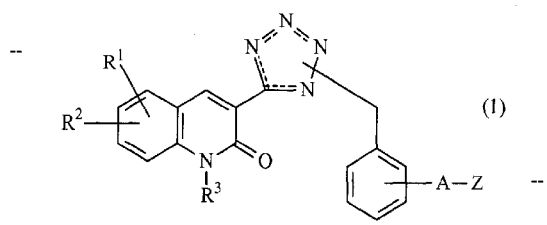
--

Column 3,
Line 1,

"
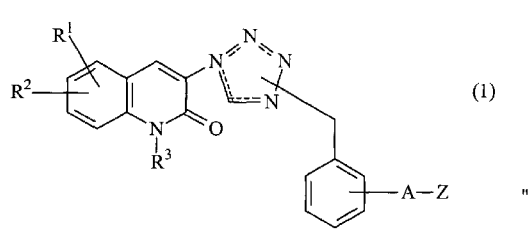

should read

--
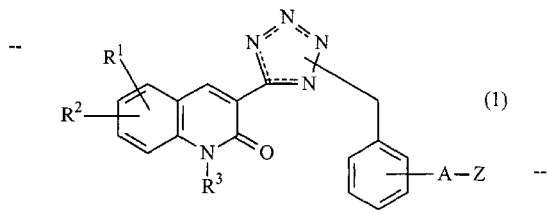
--

UNITED STATES PATENT AND TRADEMARK OFFICE
CERTIFICATE OF CORRECTION

PATENT NO.   : 6,117,886
DATED        : September 12, 2000
INVENTOR(S)  : Hendrik Timmerman et al.

It is certified that error appears in the above-identified patent and that said Letters Patent is hereby corrected as shown below:

Column 25,
Line 27,

"
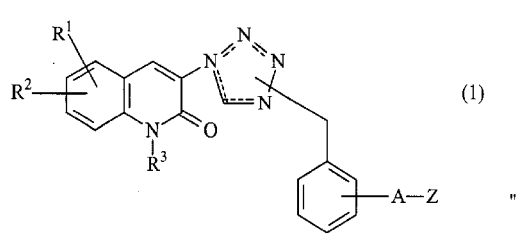
(1)

should read

--
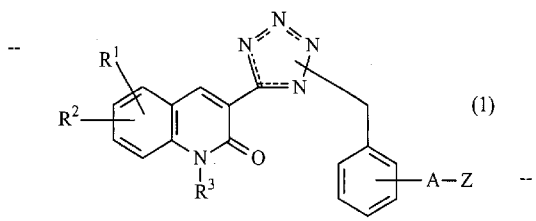
(1)
--

Signed and Sealed this

Eighth Day of July, 2003

JAMES E. ROGAN
*Director of the United States Patent and Trademark Office*